(12) United States Patent
Tsuda et al.

(10) Patent No.: US 7,266,404 B2
(45) Date of Patent: Sep. 4, 2007

(54) DEVICE FOR COLLECTING SKIN PERMEABLE GAS AND APPARATUS FOR MEASURING SKIN PERMEABLE GAS

(75) Inventors: Takao Tsuda, Nisshin (JP); Ken Naitoh, Nagoya (JP); Kazutoshi Nose, Nagoya (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 0 days.

(21) Appl. No.: 11/432,429

(22) Filed: May 12, 2006

(65) Prior Publication Data

US 2006/0206015 A1 Sep. 14, 2006

Related U.S. Application Data

(62) Division of application No. 10/450,840, filed as application No. PCT/JP01/11435 on Dec. 26, 2001.

(30) Foreign Application Priority Data

Dec. 27, 2000 (JP) ............................. 2000-396949

(51) Int. Cl.
*A61B 5/05* (2006.01)
(52) U.S. Cl. ...................................... 600/354; 600/306
(58) Field of Classification Search ................ 600/306, 600/354
See application file for complete search history.

(56) References Cited

U.S. PATENT DOCUMENTS

| | | | | |
|---|---|---|---|---|
| 1,627,974 A | * | 5/1927 | Himmerich | .................. 251/276 |
| 3,519,392 A | | 7/1970 | Caupeil | |
| 3,649,199 A | * | 3/1972 | Littlejohn | .................... 436/178 |
| 3,659,586 A | * | 5/1972 | Johns et al. | ................. 600/354 |
| 4,005,700 A | | 2/1977 | Parker | |
| 4,096,853 A | | 6/1978 | Weigand | |
| 4,287,819 A | * | 9/1981 | Emerit | ......................... 99/472 |
| 4,439,679 A | * | 3/1984 | McIlroy et al. | ............. 250/282 |
| 4,947,861 A | * | 8/1990 | Hamilton | ..................... 600/532 |
| 5,131,390 A | * | 7/1992 | Sakaguchi et al. | .......... 600/346 |
| 5,140,993 A | * | 8/1992 | Opekun et al. | ............. 600/543 |
| 5,662,677 A | * | 9/1997 | Wimmer | ...................... 606/201 |
| 5,782,871 A | | 7/1998 | Fujiwara et al. | |
| 6,287,255 B1 | * | 9/2001 | Endo et al. | ................. 600/307 |
| 7,004,909 B1 | | 2/2006 | Patel et al. | |

FOREIGN PATENT DOCUMENTS

| | | |
|---|---|---|
| JP | 2-1105 | 1/1990 |
| JP | 3-47855 | 7/1991 |
| JP | 6-119 | 1/1994 |
| JP | 2839865 | 10/1998 |
| JP | 11-318874 | 11/1999 |
| JP | 3048554 | 3/2000 |

* cited by examiner

*Primary Examiner*—Charles A. Marmor, II
*Assistant Examiner*—Karen E. Toth
(74) *Attorney, Agent, or Firm*—Oblon, Spivak, McClelland, Maier & Neustadt, P.C.

(57) ABSTRACT

An apparatus for measuring skin permeable gas, which can be used to obtain clinical information by noninvasive and bloodless operations and are useful for in-home medical care and health management. The device for collecting skin permeable gas includes a finger-stall including a coupler, and one or more connections that are connectable with the coupler and include a stopcock.

12 Claims, 11 Drawing Sheets

(a)

(b)

(c)

(d)

RELATIONSHIP 2 BETWEEN EXPIRED GAS AND LEFT HAND (SUBJECT A)

RELATIONSHIP 2 BETWEEN EXPIRED GAS AND LEFT HAND (SUBJECT B)

DEVICE FOR COLLECTING SKIN PERMEABLE GAS AND APPARATUS FOR MEASURING SKIN PERMEABLE GAS

CROSS-REFERENCE TO RELATED APPLICATIONS

The present application is a divisional of U.S. application Ser. No. 10/450,840 filed on Dec. 9, 2003, and in turn claims priority to PCT/JP01/11435 filed in the Japan Patent Office on Dec. 26, 2001, the entire contents of each of which are hereby incorporated herein by reference.

TECHNICAL FIELD

The present invention relates to a device for collecting skin permeable gas and an apparatus for measuring such skin permeable gas, wherein the device and apparatus are used to determine the health condition of subjects.

BACKGROUND ART

Conventionally, blood and human metabolites (urine and feces) have been major clinical items used for determining human health condition. Recently, saliva and expired gas have been becoming test objects, and sweat will be also included in such clinical items in future. Components of such expired gas, saliva, and sweat depend on components of blood and thus there is quantitative relationship between both the components. It is expected that these noninvasive metabolites be used in the field of in-home medical care and health management in future.

There have been no measuring equipment used for clinical measurement and no measuring equipment for determining human health condition using such skin permeable gas. This is because the existence of the skin permeable gas itself has not been assumed for such purposes.

DISCLOSURE OF INVENTION

As described above, the inventors have found that skin permeable gas depends on components of blood in peripheral blood vessels. The inventors have also found that the skin permeable gas is extremely important in determining new types of morbidity.

In view of the above situation, it is an object of the present invention to provide an apparatus for measuring the skin permeable gas, wherein such an apparatus can be used to obtain clinical information by noninvasive and bloodless operations and is useful for in-home medical care and health management.

In order to achieve the above object, the following devices and apparatus are provided.

(1) A skin permeable gas-collecting device including a container having an opening section and including a storing means for storing skin permeable gas emanating from skin, the skin permeable gas being obtained by bringing the opening section into intimate contact with the skin; and a delivery means for delivering the skin gas stored in the container.

(2) The skin permeable gas-collecting device further including a partition, disposed at a lower section inside the container, having an opening at the center thereof; and an operating member for opening and closing the opening of the partition.

(3) The skin permeable gas-collecting device, wherein container includes a first sub-container, having a hole, for storing the skin permeable gas; a second sub-container that surrounds the first sub-container and is brought into intimate contact with the skin by decompression obtained by removing air; and a delivery unit for delivering the skin permeable gas stored in the first sub-container.

(4) A skin permeable gas-collecting device including a finger-stall including a coupler, and one or more connections that are connectable with the coupler and include a stopcock.

(5) A skin permeable gas-collecting device including a cylindrical member including a spiral groove, a cover disposed on the upper surface of the cylindrical member, a gas-introducing section connected to the cover, a gas delivery section connected to the cover, and a sealing member for sealing the groove of the cylindrical member and for maintaining air contained in the groove at a predetermined temperature, wherein, after components in the air maintained at a predetermined temperature are analyzed, the sealing member is detached from the cylindrical member and the cylindrical member from which the sealing member is detached is then brought into intimate contact with skin of a subject to collect the skin permeable gas.

(6) A skin permeable gas-measuring apparatus including a first container, having an opening, for storing skin permeable gas; a blower fan for circulating the stored skin permeable gas; and a measuring unit including a coloring agent placed in a path through which the gas is circulated with the blower fan.

BEST MODE FOR CARRYING OUT THE INVENTION

Embodiments of the present invention will now be described in detail with reference to the accompanying drawings.

Figure 1:
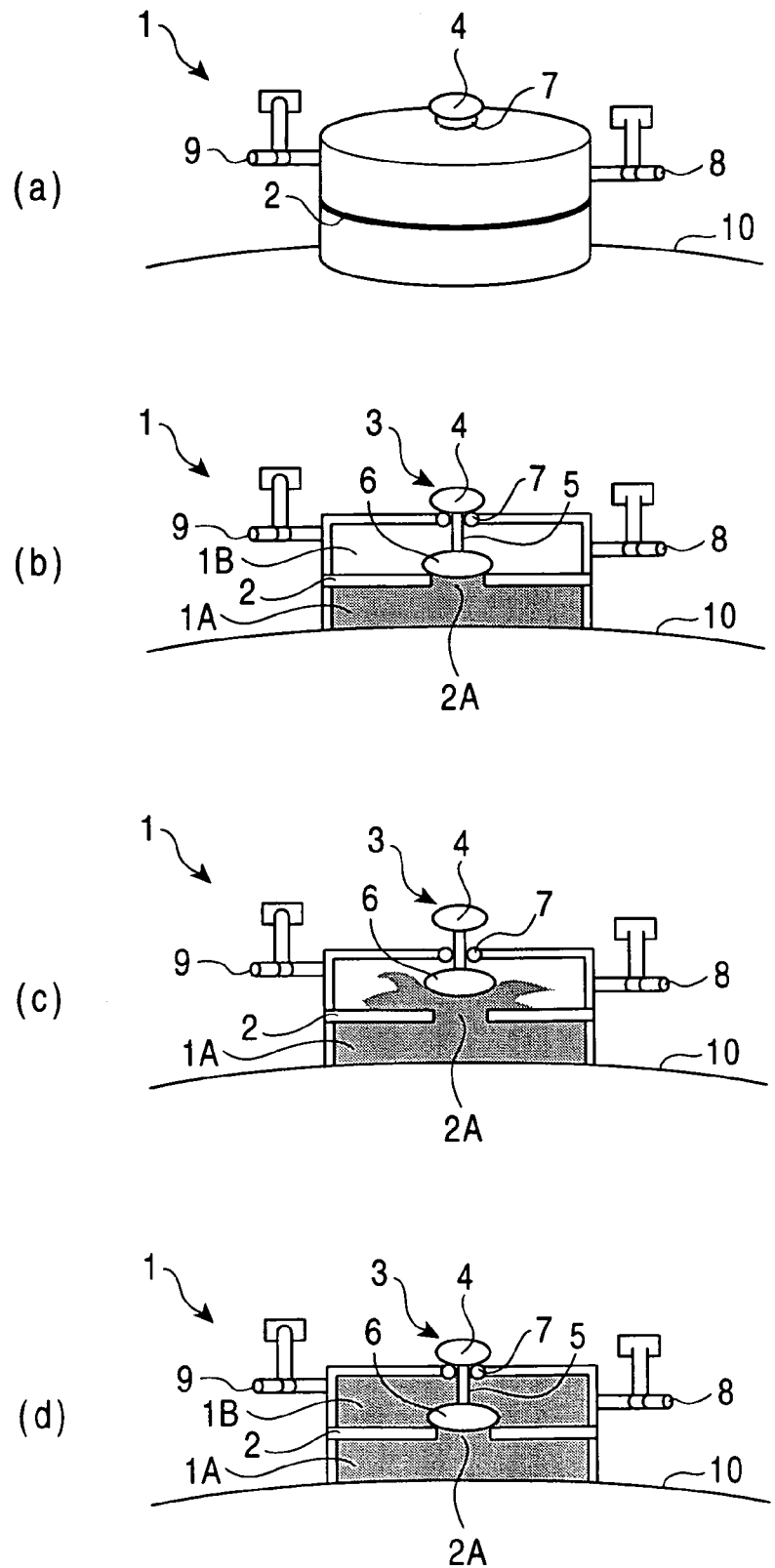
FIG. 1 is an illustration showing a configuration of a skin permeable gas-collecting device according to a first example of the present invention.

FIG. 1 is an illustration showing a configuration of a skin permeable gas-collecting device according to a first example of the present invention. FIG. 1(a) is a perspective view showing the outline thereof, FIG. 1(b) is an illustration showing such a state that a lower chamber of the skin permeable gas-collecting device is filled with skin permeable gas, FIG. 1(c) is an illustration showing such a state that the skin permeable gas is allowed to flow into an upper chamber from the lower chamber, and FIG. 1(d) is an illustration showing such a state that the upper chamber filled with the skin permeable gas is sealed.

In these figures, reference numeral 1 represents a container of the skin permeable gas-collecting device; reference numeral 1A represents a lower chamber disposed in the container 1; reference numeral 1B represents an upper chamber disposed in the container 1; reference numeral 2 represents a partition plate, disposed at a lower position inside the container 1, having an opening 2A at the center thereof; reference numeral 3 represents an operating member capable of opening and closing the opening 2A of the partition plate 2; reference numeral 4 represents a knob disposed at the upper end of the operating member 3; reference numeral 5 represents a rod of the operating member 3; reference numeral 6 represents a valve member disposed at the lower end of the rod 5; reference numeral 7 represents an O-ring for sealing a gap between the container 1 and the rod 5; reference numeral 8 represents a ventilation port, connected to the container 1, for removing the skin permeable gas; reference numeral 9 represents a delivery port, connected to the container 1, for removing the skin permeable gas; and reference numeral 10 represents skin of a subject.

The operation of this device is described below.

As shown in FIG. 1(b), the container 1 of the skin permeable gas-collecting device is pressed against the subject skin 10 and then fixed thereto in such a state that the operating member 3 is pressed downward and thereby the opening 2A of the partition plate 2 is stopped up with the valve member 6. In such a state, skin permeable gas emanating from the subject skin 10 is collected in the lower chamber 1A. The ventilation port and the delivery port 9 for removing the skin permeable gas are closed, wherein the ventilation port and the delivery port 9 are connected to the container 1.

After the collection of the skin permeable gas is finished, the operating member 3 is drawn up to open the opening 2A of the partition plate 2, as shown in FIG. 1(c). Thereby, the skin permeable gas collected in the lower chamber 1A is allowed to flow into the upper chamber 1B.

As shown in FIG. 1(d), the operating member 3 is pressed down again to close the opening 2A of the partition plate 2 and thereby the skin permeable gas is trapped and stored in the upper chamber 1B.

The delivery port 9 for the skin permeable gas is opened, the ventilation port 8 is also opened, and gas is fed from the ventilation port 8 to force the skin permeable gas out, thereby subjecting the skin permeable gas to measurement. This procedure, however, is not shown in the figure.

Figure 2:
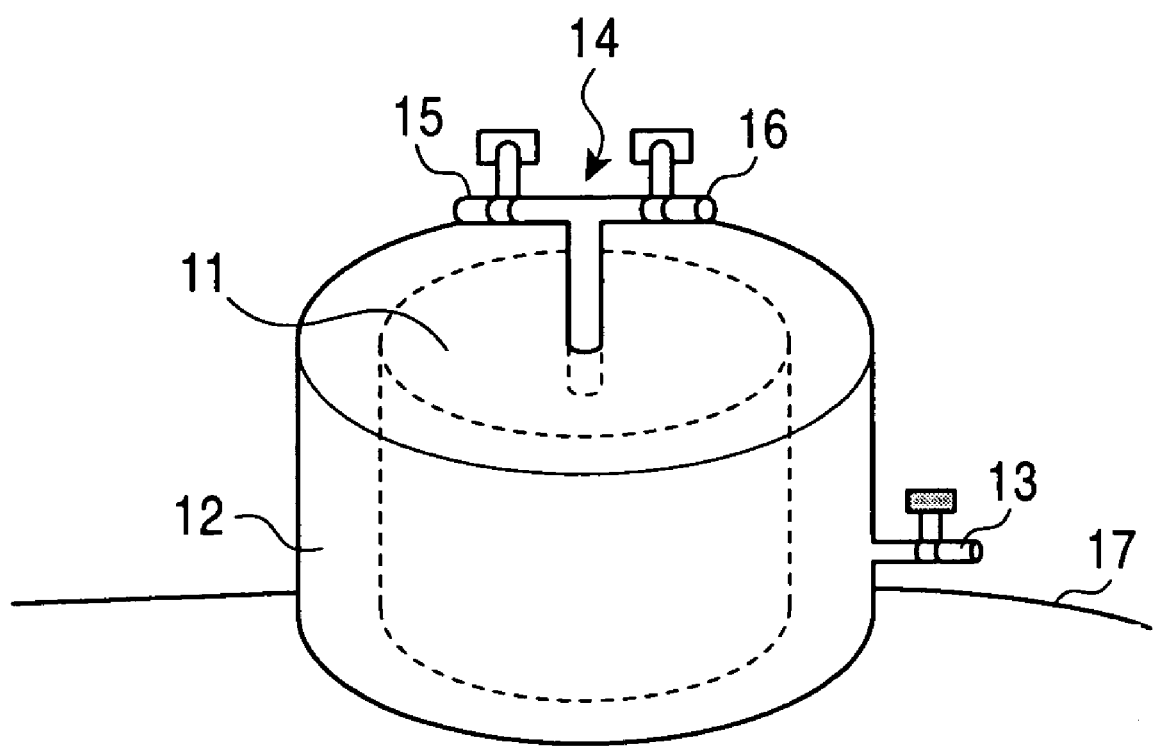
FIG. 2 is an illustration showing a configuration of a skin permeable gas-collecting device according to a second example of the present invention.

FIG. 2 is an illustration showing a configuration of a skin permeable gas-collecting device according to a second example of the present invention.

In this figure, reference numeral 11 represents a first container for storing the skin permeable gas; reference numeral 12 represents a second container, surrounding the first container 11 for removing air to provide decompression to bring the first container 11 into intimate contact with skin; reference numeral 13 represents an evacuation unit, connected to the second container 12, for removing gas; reference numeral 14 represents a cock; reference numeral 15 represents a gas-introducing unit connected to the first container 11; reference numeral 16 represents a delivery unit, connected to the first container 11, for removing the skin permeable gas; and reference numeral 17 represents skin of a subject.

According to the above configuration, after the delivery unit 16 is closed and the gas-introducing unit 15 is opened to introduce gas (dry air) into the first container 11, the gas-introducing unit 15 is closed to collect the skin permeable gas from the subject skin 17. After the skin permeable gas is collected, the delivery unit 16 is opened to deliver the skin permeable gas into a test container (not shown).

In this case, in order to bring the first container 11 into intimate contact with the subject skin 17, the container section has dual structure. In particular, the second container 12 arranged outside the first container 11 is decompressed with the evacuation unit 13, thereby bringing the first container 11 into intimate contact with the skin.

Figure 3:
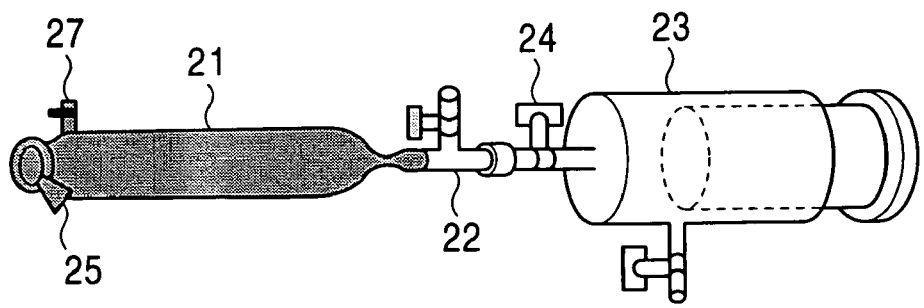
FIG. 3 is an illustration showing a configuration of a skin permeable gas-collecting device according to a third example of the present invention.
Figure 3:
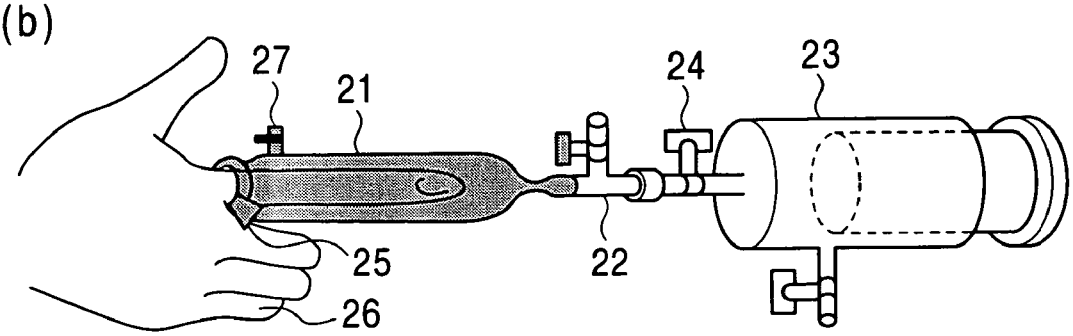
Figure 3:
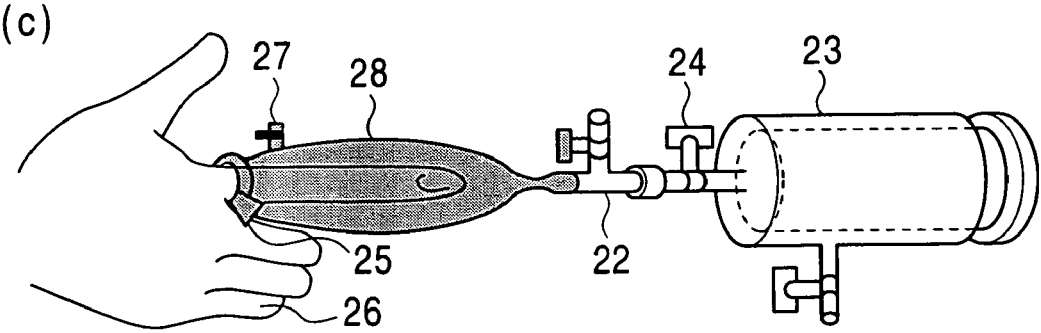
Figure 3:
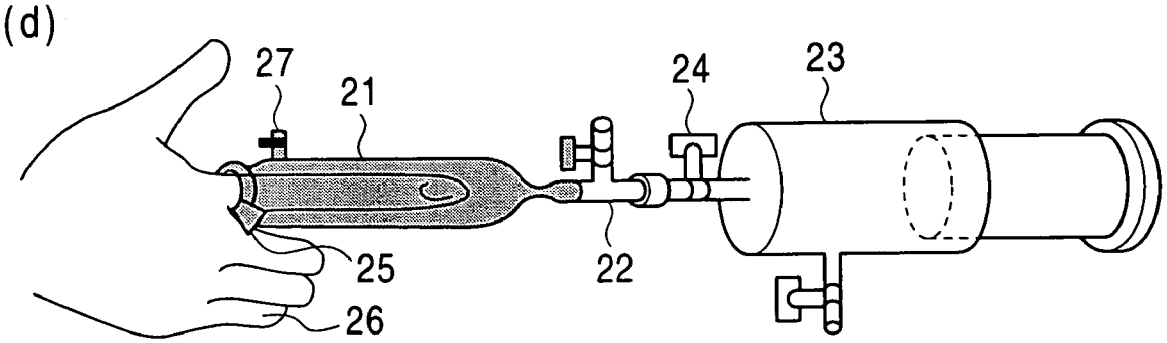

FIG. 3 is an illustration showing a configuration of a skin permeable gas-collecting device according to a third example of the present invention. FIG. 3(a) is an illustration showing a finger-stall and an injection syringe connected thereto, FIG. 3(b) is an illustration showing such a situation that a finger is fitted into the finger-stall, FIG. 3(c) is an illustration showing such a situation that the finger-stall is filled with air fed from the injection syringe, and FIG. 3(d) is an illustration showing such a situation that the air and skin permeable gas are inhaled.

In these figures, reference numeral 21 represents a finger-stall (a bag made from Teflon), reference numeral 22 represents a coupler (for example, a cock), reference numeral 23 represents an injection syringe (100 ml ), reference numeral 24 represents a stopcock, reference numeral 25 represents rubber or a clip provided on the outside of the base of the finger-stall 22, reference numeral 26 represents a finger of a subject, reference numeral 27 represents a gas-introducing unit, and reference numeral 28 represents the inflated finger-stall filled with air.

According to this example, the skin permeable gas can be recovered by the following methods.

(1) First Method

As shown in FIG. 3(a), the following tools are prepared: the finger-stall 21 having the cock 22 at the tip thereof and the injection syringe 23, connectable to the cock 22, including the stopcock 24. As shown in FIG. 3(b), the finger 26 is fitted into the finger-stall 21. As shown in FIG. 3(*c*), the stopcock 24 is opened, the cock 22 is then opened to introduce gas (dry air) from the injection syringe 23, the finger-stall 21 is inflated and then sealed, and the stopcock 24 is then closed. Subsequently, the skin permeable gas is collected from the subject finger 26. After the collection of the skin permeable gas, the stopcock 24 is opened to deliver (recover) the collected skin permeable gas into injection syringe 23 through the cock 22.

(2) Second Method

As shown in FIG. 3(*a*), the following tools are prepared: the finger-stall 21 having the cock 22 at the tip thereof and the injection syringe 23, connectable to the cock 22, including the stopcock 24. As shown in FIG. 3(*b*), the finger 26 is fitted into the finger-stall 21. As shown in FIG. 3(*c*), the stopcock 24 is closed, the gas-introducing unit 27 is opened to introduce gas (dry air), the finger-stall 21 is inflated and then sealed, thereby collecting the skin permeable gas. After the collection of the skin permeable gas, the stopcock 24 is opened to recover the collected skin permeable gas into injection syringe 23 through the cock 22.

(3) Third Method

As shown in FIG. 3(*a*), the following tools are prepared: the finger-stall 21 having the cock 22 at the tip thereof and the injection syringe 23, connectable to the cock 22, including the stopcock 24. As shown in FIG. 3(*b*), the finger 26 is fitted into the finger-stall 21. As shown in FIG. 3(*c*), the stopcock 24 is opened, and the skin permeable gas is collected in the injection syringe 23 while the gas-introducing unit 27 is opened to introduce gas (dry air).

The collecting procedure is not limited to the above methods. Various modifications including the following procedures may be performed: a procedure in which gas is introduced from the cock 22 to collect the skin permeable gas and the skin permeable gas is then recovered (delivered) into the injection syringe 23 and a procedure in which gas is introduced from the gas-introducing unit 27 to collect the skin permeable gas and the skin permeable gas is then recovered through the cock 22.

According to the above configuration, emitted gas can be readily collected from the body skin surface, for example, the finger skin surface, which is herein used, and then recovered (delivered).

Examples according to the collecting procedure will now be described.

Figure 4:
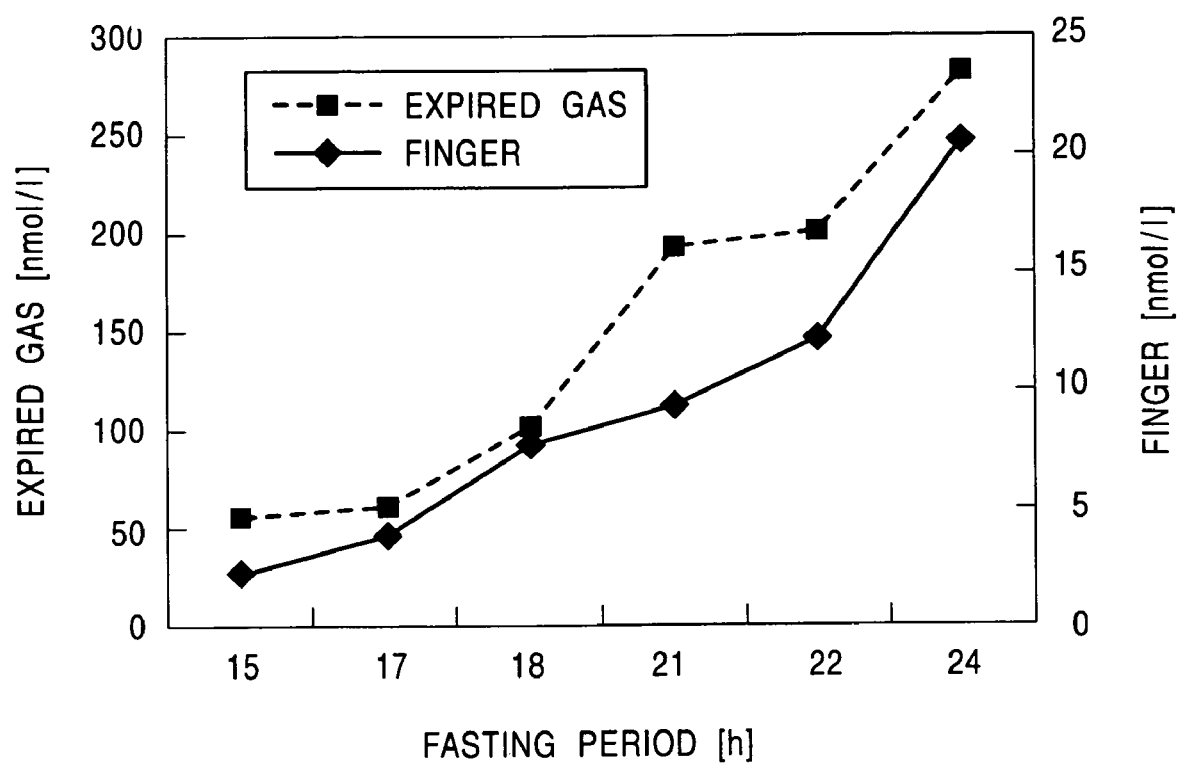
FIG. 4 is an illustration showing a comparison between the acetone content in expired gas and the acetone content in vapor emanating from a left index finger.

FIG. 4 is an illustration showing a comparison between the acetone content in expired gas and the acetone content in vapor emanating from a left index finger.

Acetone emanating from the left index finger was collected and the expired gas was also collected at the time when the acetone sampling is stated. The comparison result of the acetone content is shown in FIG. 4. As shown in this figure, there is a positive correlation between the acetone content in the expired gas and the acetone content in the vapor emanating from the left index finger.

When the acetone emanating from the left index finger was collected according to the above procedure and then determined, the outside air was used in this procedure. This is because the outside air inevitably leaks into the finger-stall when the finger is fitted into the finger-stall during the sampling.

This procedure was employed on the premise that the acetone content in the outside air does not change for a short period (within 30 minutes). Since the acetone content does not inevitably remain constant in actual, this procedure for determining the acetone content is not precise if a change in the acetone content exceeds allowable limits. In order to solve this problem, the following finger-stall and sampling procedure must be employed: a finger-stall into which the outside air does not leak when a finger is fitted into or drawn out of the finger-stall, and a sampling procedure using such a finger-stall.

Figure 5:
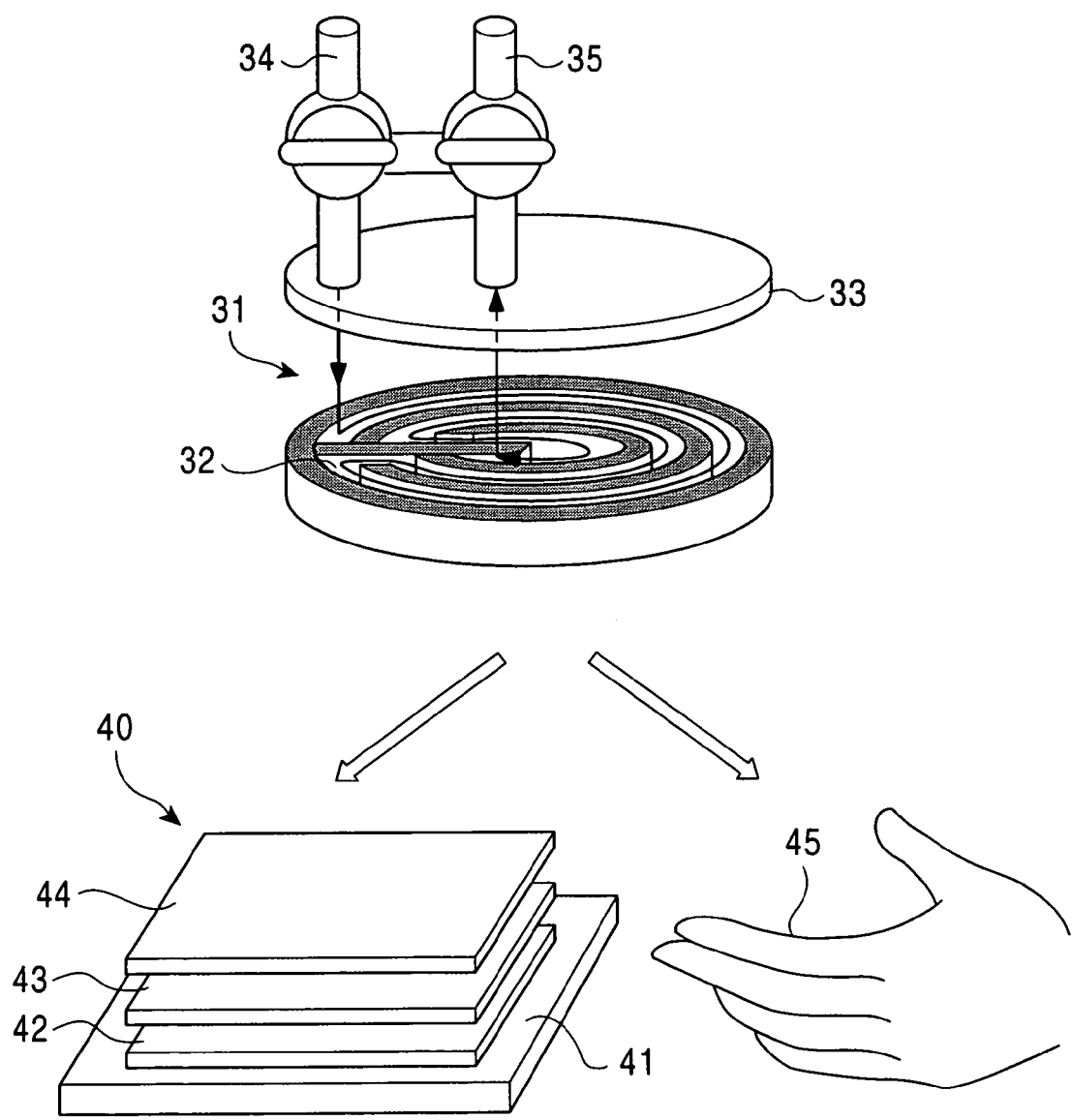
FIG. 5 is an illustration showing a configuration of a skin permeable gas-collecting device (sampling probe) according to a fourth example of the present invention.

FIG. 5 is an illustration showing a configuration of a skin permeable gas-collecting device (sampling probe) according to a fourth example of the present invention.

In this figure, reference numeral 31 represents a cylindrical member having a spiral groove 32; reference numeral 33 represents a cover placed on the upper face of the cylindrical member 31; reference numeral 34 represents a gas-introducing section connected to the cover 33; reference numeral 35 represents a gas delivery section connected to the cover 33; reference numeral 40 represents a sealing member, connected to the cylindrical member, for sealing the groove 32 of the cylindrical member 31 and for maintaining air contained in the groove 32 at a predetermined temperature; reference numeral 41 represents a heat sink; reference numeral 42 represents a Peltier element for adjusting the temperature of the contained air; reference numeral 43 represents a silicon coating; and reference numeral 44 represents a Teflon sheet for sealing the groove 32 containing the air.

Air in a laboratory room is introduced into the cylindrical member 31 from the gas-introducing section 34 and then stored therein, the temperature of the introduced air is adjusted to a predetermined value with the Peltier element 42, and the resulting air is delivered through the gas delivery section 35, thereby subjecting the air (probe blank) to measurement. Replacing the sealing member 40 connected to the cylindrical member in the situation, the bottom face of the cylindrical member 31 is pressed against skin of a subject 45 to collect skin permeable gas in the groove 32 of the cylindrical member 31 in a sealed manner while the above situation is maintained except that the sealing member 40 of the cylindrical member is not used. The collected skin permeable gas is delivered together with air through the gas delivery section 35 and is then subjected to measurement.

The measurement result is described below.

Table 1 shows the measurement result.

| Human | Value Obtained from Measuring Tool (Air Only) | Value Obtained from Human Skin (Air + Skin Permeable Gas) | Actual Quantity Obtained from Human Skin |
|---|---|---|---|
| a | 1.8 | 4.4 | 2.6 |
| b | 3.3 | 7.6 | 4.3 |
| c** | 3.1 | 11.7 | 8.6 |
| d** | 4.5 | 14.0 | 9.5 |
| e** | 3.9 | 9.1 | 5.2 |
| f | 4.9 | 7.7 | 2.8 |
| g** | 2.0 | 12.6 | 10.6 |

As shown in this table, for Subject a, the air quantity obtained from a measuring tool is 1.8 ng, and the total quantity of air and acetone is 4.4 ng, the acetone being skin permeable gas emanating from the subject. Thus, the quantity of acetone gas emanating from the skin surface of the subject is 2.6 ng. In any subject, sampling data obtained from skin has a higher value than that of the probe blank.

The acetone content in 50 ml, 25 ml, and 10 ml of room air is 5.8, 2.8, and 1.3 ng, respectively. Since the volume of the sampling probe is 3.8 ml, the quantity of contaminants leaking from the surroundings is 0.5 ng or less. The acetone content in air of the laboratory room is substantially equal to that in room air in a reinforced concrete building.

It can be inferred from the above result that the quantity of acetone emanating from a human skin surface can be measured with this experiment means.

Figure 6:
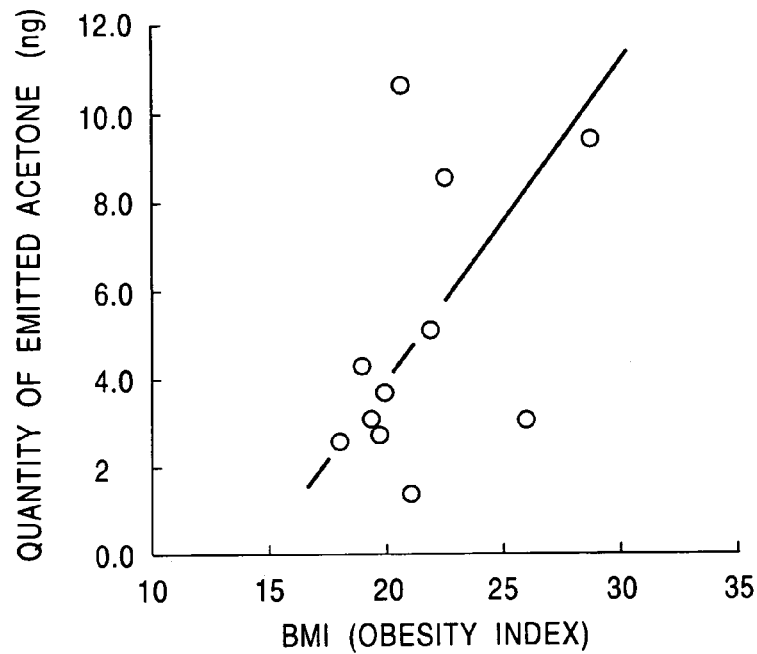
FIG. 6 is an illustration showing the relationship between the quantity of emitted acetone and BMI, wherein the acetone quantity is obtained with a device of the present invention and BMI is an obesity index.

FIG. 6 is an illustration showing the relationship between the quantity of emitted acetone and BMI (body mass index, defined as the formula: body weight (kg)/(body height (m))$^2$), wherein the acetone quantity is obtained with a device of the present invention and BMI is an obesity index.

It is clear from this figure that there is a positive correlation between the obesity index (BMI) and the quantity of emitted acetone.

Gas collected from a human skin surface is analyzed by, for example, chromatography.

Figure 7:
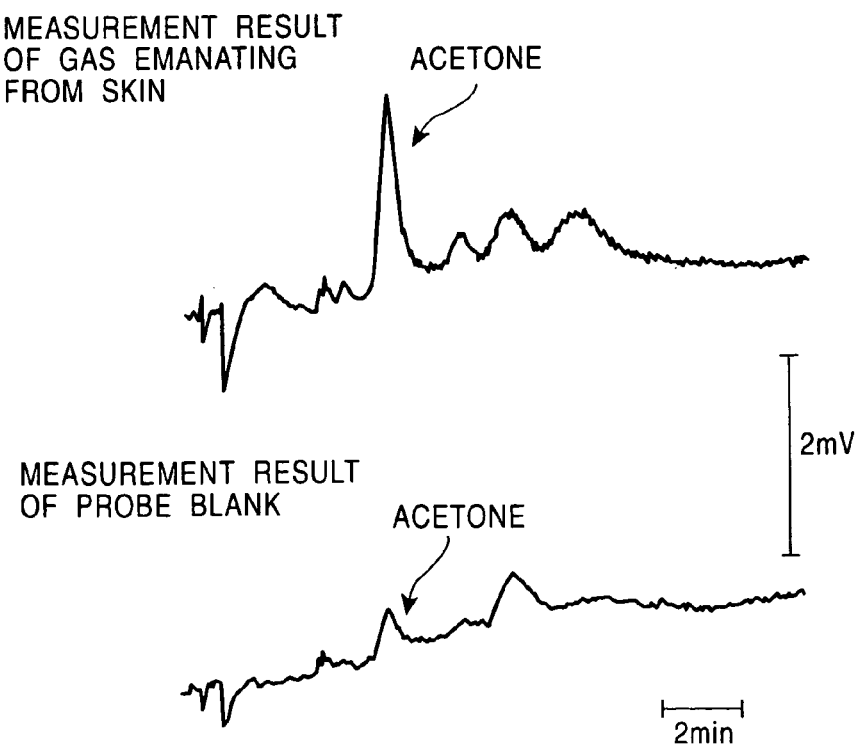
FIG. 7 is an illustration showing chromatograms of a probe blank of the present invention which is obtained by performing sampling inside a left forearm for ten minutes.

FIG. 7 is an illustration showing the result of chromatography analysis of a probe blank of the present invention which is obtained by performing sampling inside a left forearm for one minute. The upper section of FIG. 7 is an illustration showing the result of the chromatography analysis of gas obtained by performing sampling inside a left forearm for ten minutes using a skin permeable gas-collecting device of the present invention. The lower section of FIG. 7 is an illustration showing the result of the chromatography analysis of the probe blank. It is clear from this figure that the quantity of the skin permeable gas emanating from the human skin surface is larger than that of the gas remaining in the surroundings and the probe blank.

FIGS. 8 to 11 are illustrations showing the relationship between the ingestion of milk and the quantity of emitted hydrogen gas collected with a skin permeable gas-collecting device of the present invention; between the ingestion of milk and the quantity of the hydrogen gas in expired gas after the ingestion of milk. The illustrations show chromatograms obtained by measuring the hydrogen content in the following cases: an expired gas and a gas obtained from the left hand of Subject A (before the drinking of milk and after four hours following the drinking of the milk) and an expired gas and a gas obtained from the left hand of Subject B (before the drinking of milk and after four hours following the drinking of the milk).

Figure 8:
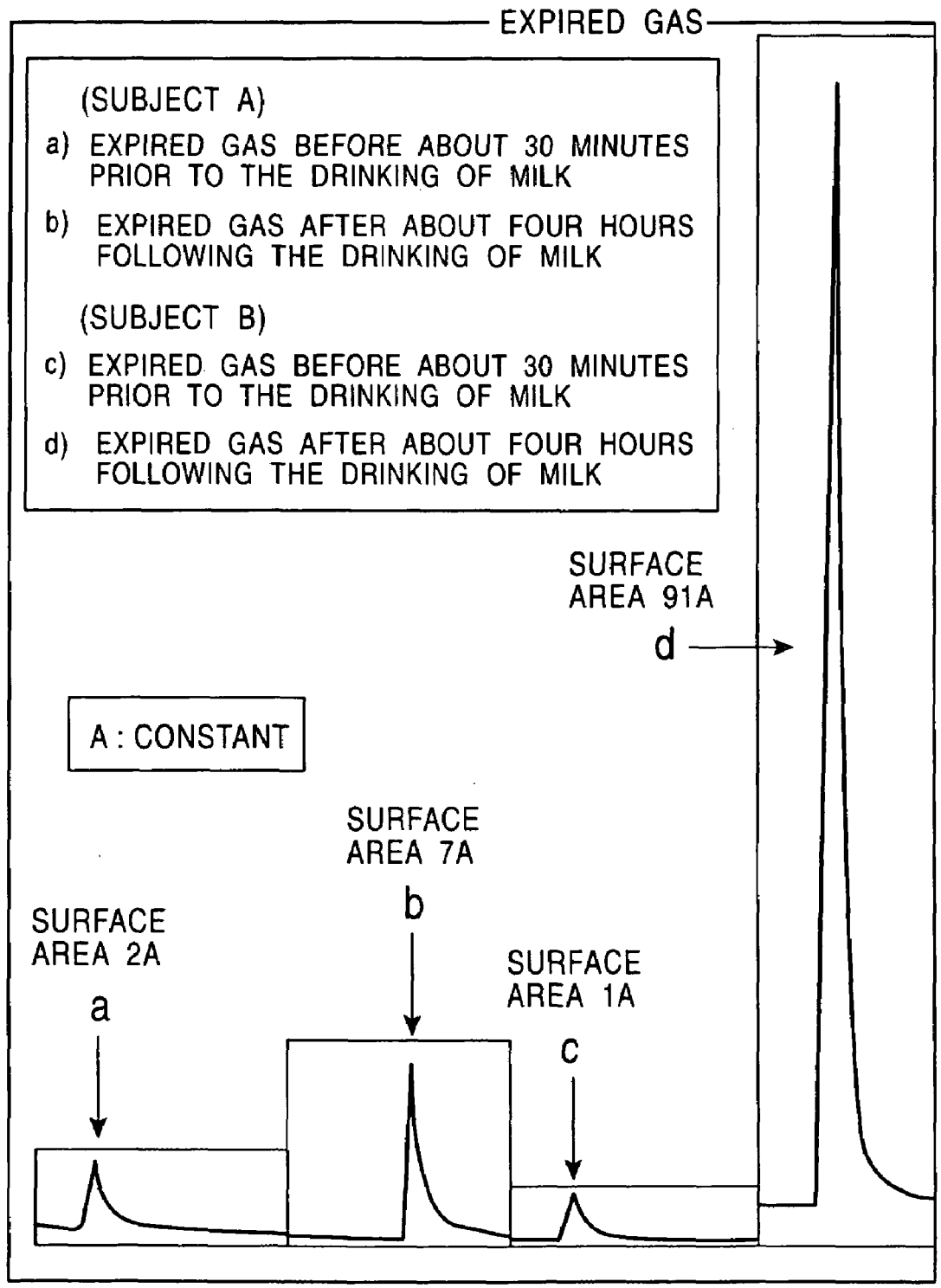
FIG. 8 is an illustration (first illustration) showing the relationship between the ingestion of milk and the quantity of emitted hydrogen gas collected with a skin permeable gas-collecting device of the present invention; between the ingestion of milk and the quantity of the hydrogen gas in expired gas after the ingestion of milk.

FIG. 8 is an illustration showing chromatograms of hydrogen contained in expired gas. Chromatogram a is obtained by measuring the hydrogen content in expired gas of Subject A before the drinking of milk, and Chromatogram b is obtained by measuring the hydrogen content in expired gas of Subject A after the drinking of milk. In FIG. 8, Chromatograms (a) and (c) are obtained with a sensitivity of 5 mV and Chromatograms (b) and (d) are obtained with a sensitivity of 100 mV.

Figure 9:
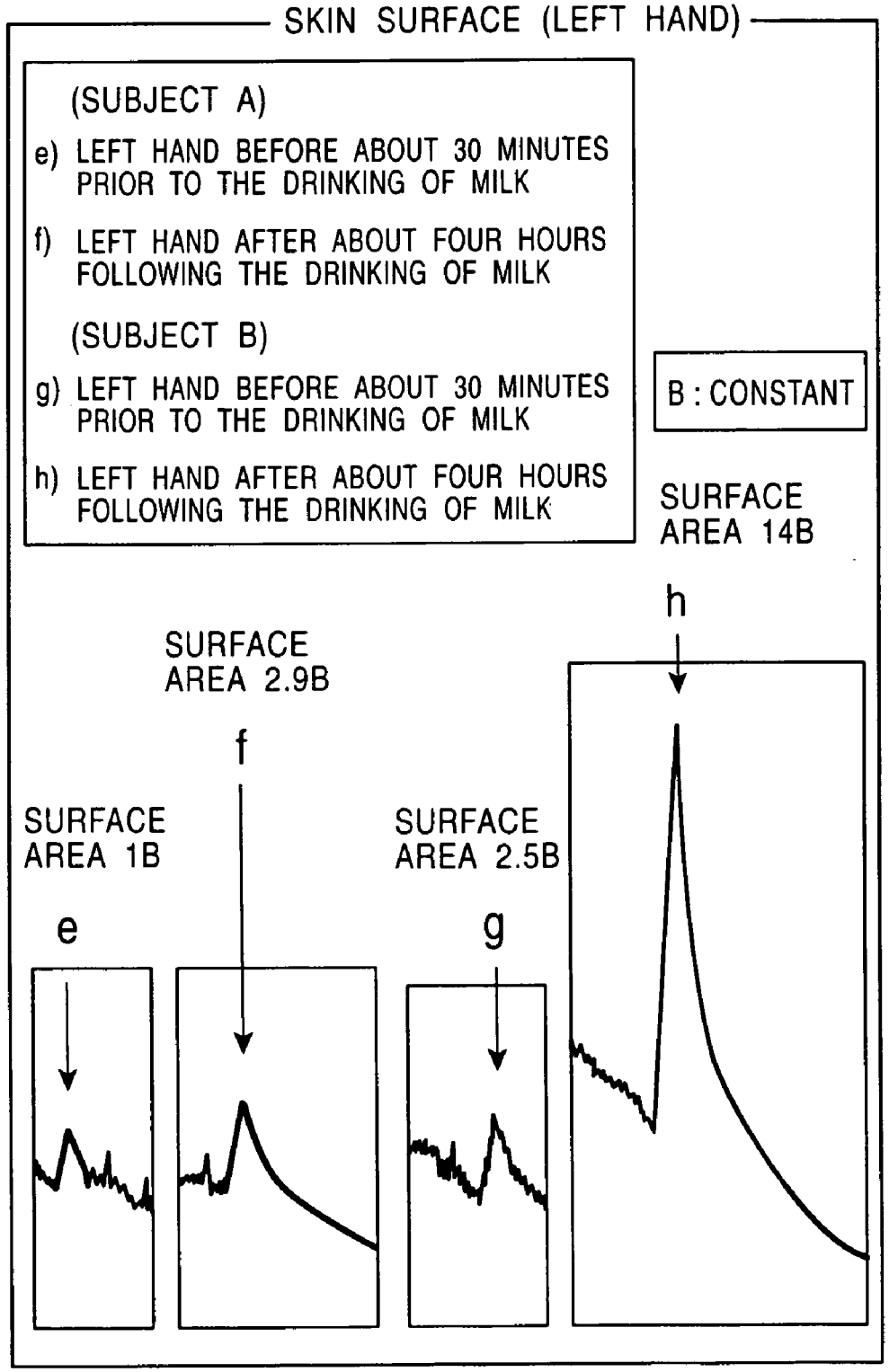
FIG. 9 is an illustration (second illustration) showing the relationship between the ingestion of milk and the quantity of emitted hydrogen gas collected with a skin permeable gas-collecting device of the present invention; between the ingestion of milk and the quantity of the hydrogen gas in expired gas after the injection of milk.

FIG. 9 is an illustration showing the analysis results of skin permeable gas obtained from left hands for ten minutes. The gas was obtained after about four hours since subjects had drunk milk. In FIG. 9, the sensitivity is 2 mV.

It is clear from these figures that human skin surface emanates hydrogen and the hydrogen can be detected using a device of the present invention. It is found that the correlation between the ingest of milk and the hydrogen emanation can be clarified.

When the hydrogen content in gas obtained before the drinking of milk is compared with the hydrogen content in gas obtained after about four hours following the drinking of milk, the following results are obtained: the hydrogen content in expired gas of Subject A increases from 2 to 7 ppm, the hydrogen content in expired gas of Subject B increases from 1 to 91 ppm, the hydrogen content in gas emanating from the left hand of Subject A increases from 0.003 to 0.08 ppm, and the hydrogen content in gas emanating from the left hand of Subject B increases from 0.07 to 0.41 ppm. Thus, it is clear that an increase in hydrogen in not only expired gas but also gas emanating from a left hand is caused by the drinking of milk. Furthermore, it is clear from this measurement that there is an extremely high correlation between the hydrogen content in expired gas and the hydrogen content in gas emanating from skin.

Figure 10:
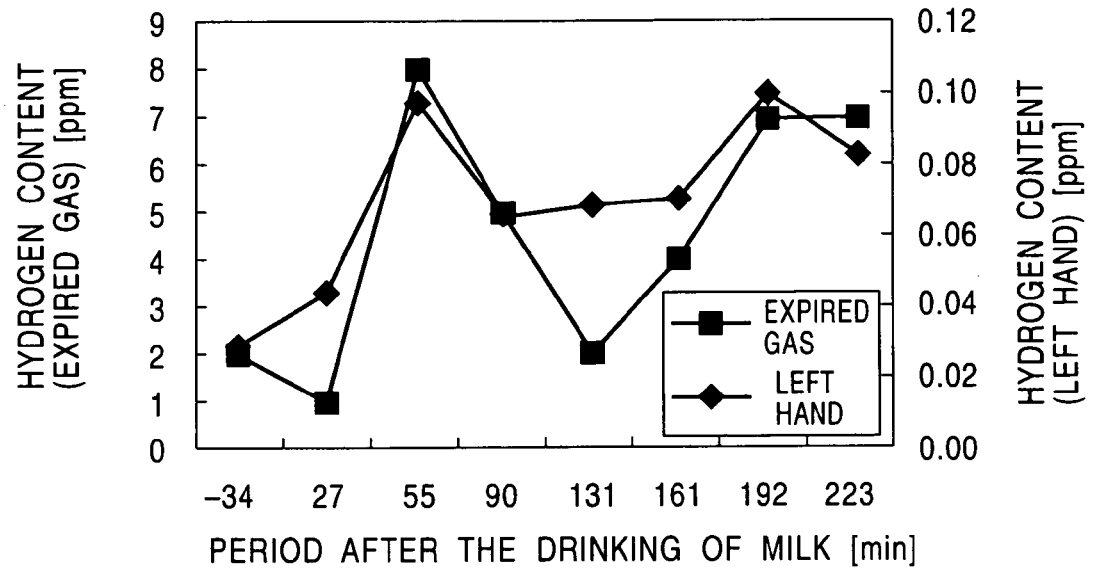
FIG. 10 is an illustration (third illustration) showing the relationship between the ingestion of milk and the quantity of emitted hydrogen gas collected with a skin permeable gas-collecting device of the present invention; between the ingestion of milk and the quantity of the hydrogen gas in expired gas after the ingestion of milk.
Figure 10:
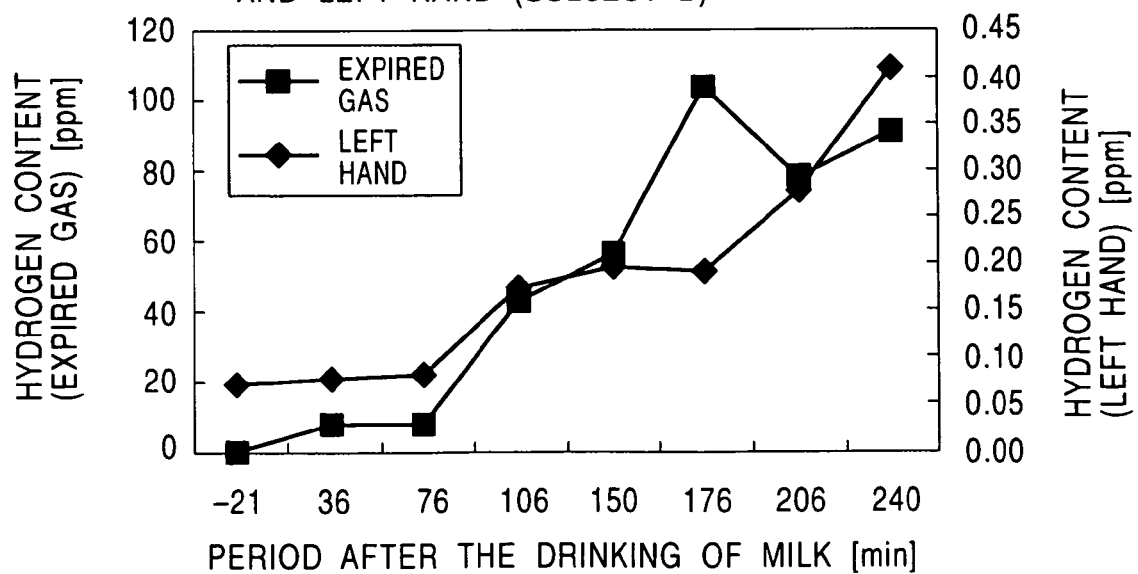
Figure 11:
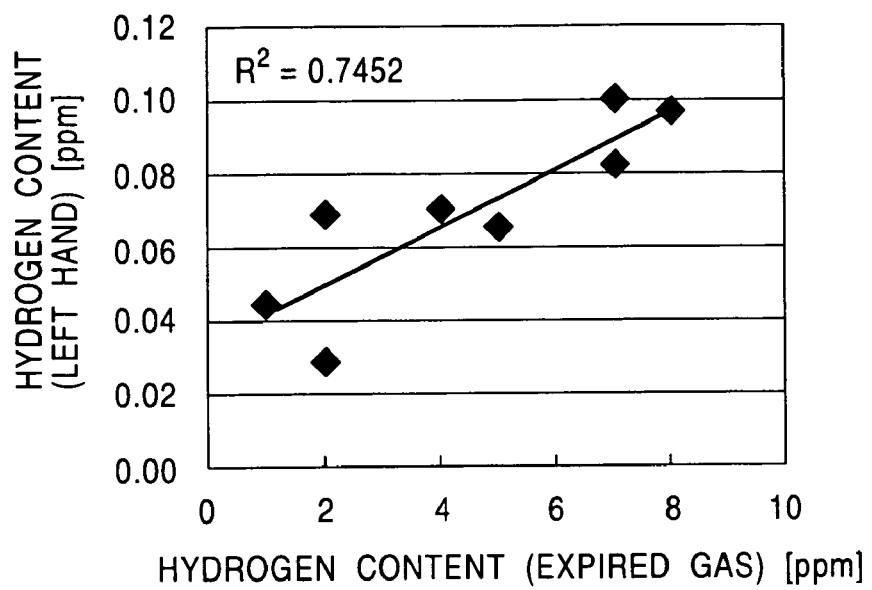
FIG. 11 is an illustration (fourth illustration) showing the relationship between the ingestion of milk and the quantity of emitted hydrogen gas collected with a skin permeable gas-collecting device of the present invention; between the ingestion of milk and the quantity of the hydrogen gas in expired gas after the ingestion of milk.
Figure 11:
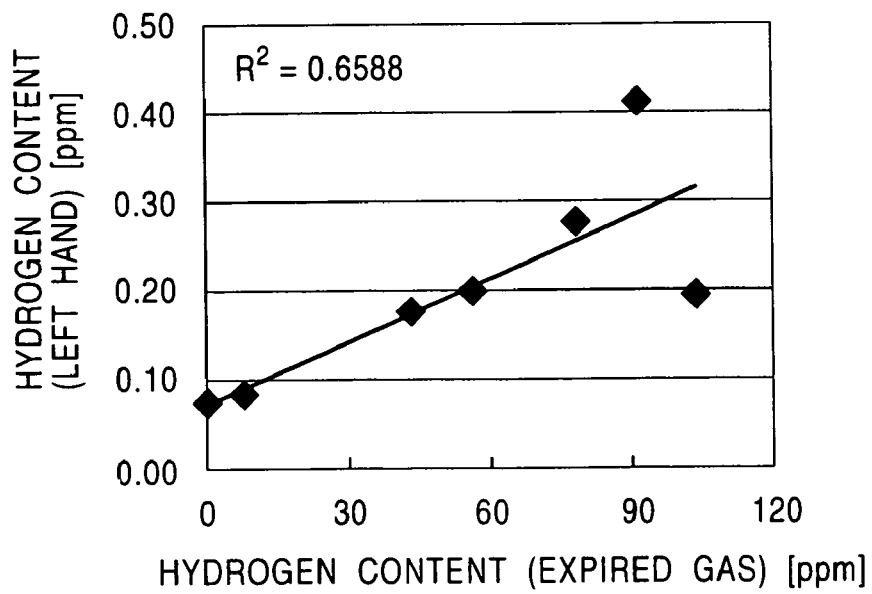

FIGS. 10 and 11 are illustrations showing a correlation between expired gas and skin permeable gas. There is a obvious correlation for hydrogen, which suggests that diagnosis using the skin permeable gas is possible.

Figure 12:
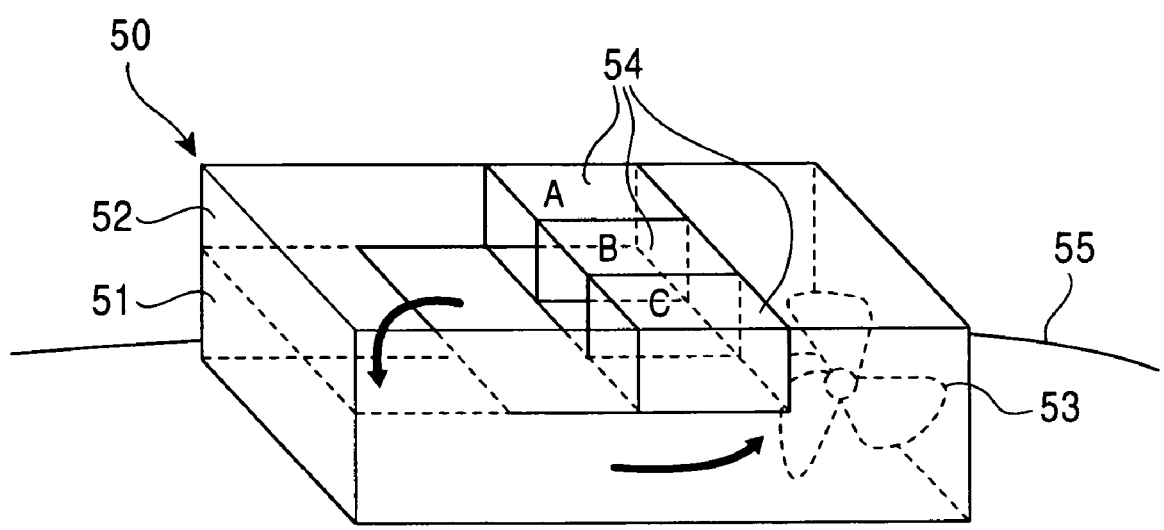
FIG. 12 is an illustration showing a configuration of a skin permeable gas-measuring apparatus according to a fifth example of the present invention.

FIG. 12 is an illustration showing a configuration of a skin permeable gas-measuring apparatus according to a fifth example of the present invention.

In this figure, reference numeral 50 represents a skin permeable gas-measuring apparatus, reference numeral 51 represents a skin permeable gas-collecting chamber, reference numeral 52 represents a circulating chamber, reference numeral 53 represents a blower fan, reference numeral 54 represents various coloring agents A, B, C, and reference numeral 55 represents skin of a subject.

As shown in this figure, skin permeable gas is collected on the skin 55, the collected skin permeable gas is then immediately circulated to allow the gas to pass through the various coloring agents 54, thereby detecting specific gas. Thus, the subject can obtain the measurement result on the spot.

Information processing of a sampling detection system disposed on skin can be performed with a computer, which is not shown.

In order to prevent gas from being absorbed in $H_2O$ in sweat, gas replacement is sufficiently performed. That is, it is critical that used gas is removed by ventilation and sample gas is collected while the sample gas is successively discharged.

The use of the present invention is described below.

A correlation between skin permeable gas and morbidity is as follows. The skin permeable gas has a correlation with diabetes, obesity, and autointoxication when the skin permeable gas is acetone, and the skin permeable gas has a quantitative correlation with the presence of enteric bacteria that decompose lactose when the skin permeable gas is hydrogen. Furthermore, the skin permeable gas has a correlation with uremia, liver failure, abdominal abscess, and the presence of *helicobacter pylori* when the skin permeable gas is ammonia. As described above, the measurement of the skin permeable gas according to the present invention can be contribute to the diagnosis of various types of morbidity.

It should be understood that the present invention is not limited to the above examples and various modifications may be performed within the scope of the present invention. The present invention is intended to cover such modifications.

As described above in detail, according to the present invention, the following advantages can be obtained.

(A) Clinical information that are useful for in-home medical care and health management can be obtained by noninvasive and bloodless operations.

(B) Skin permeable gas emanating from skin surface can be readily collected and the species and quantity of such gas can be analyzed.

(C) Collected gas can be readily stored in a sealed manner and then transported to a measuring apparatus.

(D) Secure attachment to skin is possible.

(E) Contaminants contained in the space of a cylindrical member and/or leaking from the surroundings can be measured in advance and therefore the skin permeable gas can be precisely analyzed.

(F) When a spiral groove is placed, the quantity of collected gas per unit area of skin can be increased and thus the skin permeable gas can be efficiently collected.

(G) The miniaturization of a device and apparatus is possible.

INDUSTRIAL APPLICABILITY

As described above, a skin permeable gas-collecting device and skin permeable gas-measuring apparatus of the present invention are useful for clinical measurement using skin permeable gas and useful in determining human health condition. Such a device and apparatus can be miniaturized and are fit for the simple diagnosis of various types of morbidity.

The invention claimed is:

1. A device for collecting skin permeable gas, comprising:
   (a) a finger-stall configured to have a finger inserted thereto;
   (b) a collection device to collect gas from the finger-stall; and
   (c) one or more connections that are connectable between the finger-stall and the collection device and that include a stopcock,
   wherein the finger-stall includes a bag into which the finger is inserted.

2. The device according to claim 1, wherein the collection device includes an injection syringe.

3. A device for collecting skin permeable gas, comprising:
   (a) a finger-stall configured to have a finger inserted thereto;
   (b) a collection device to collect gas from the finger-stall; and
   (c) one or more connections that are connectable between the finger-stall and the collection device and that include a stopcock,
   wherein the one or more connections include a coupler connected to the finger-stall, and the stopcock is connected between the coupler and the collection device.

4. The device according to claim 1, wherein the one or more connections include a coupler connected to the finger-stall, and the stopcock is connected between the coupler and the collection device.

5. A device for collecting skin permeable gas, comprising:
   (a) a finger-stall configured to have a finger inserted thereto;
   (b) a collection device to collect gas from the finger-stall; and
   (c) one or more connections that are connectable between the finger-stall and the collection device and that include a stopcock,
   wherein the collection device includes an injection syringe, and
   wherein the one or more connections include a coupler connected to the finger-stall, and the stopcock is connected between the coupler and the collection device.

6. The device according to claim 2, wherein the one or more connections include a coupler connected to the finger-stall, and the stopcock is connected between the coupler and the collection device.

7. The device according to claim 1, wherein the finger-stall includes a gas-introducing unit.

8. The device according to claim 2, wherein the finger-stall includes a gas-introducing unit.

9. The device according to claim 3, wherein the finger-stall includes a gas-introducing unit.

10. The device according to claim 4, wherein the finger-stall includes a gas-introducing unit.

11. The device according to claim 5, wherein the finger-stall includes a gas-introducing unit.

12. The device according to claim 6, wherein the finger-stall includes a gas-introducing unit.

* * * * *